(12) United States Patent
Fralic

(10) Patent No.: US 7,640,177 B2
(45) Date of Patent: Dec. 29, 2009

(54) METHOD AND APPARATUS FOR DETERMINING AN OPTIMAL SHARING MIX IN A SHARED PRESCRIPTION SAVINGS PLAN

(76) Inventor: Donald R. Fralic, 100 Oxford Dr., Suite 710, Monroeville, PA (US) 15146

( * ) Notice: Subject to any disclaimer, the term of this patent is extended or adjusted under 35 U.S.C. 154(b) by 1877 days.

(21) Appl. No.: 10/609,995

(22) Filed: Jun. 30, 2003

(65) Prior Publication Data

US 2004/0024617 A1 Feb. 5, 2004

Related U.S. Application Data

(63) Continuation-in-part of application No. 10/121,472, filed on Apr. 11, 2002.

(60) Provisional application No. 60/283,000, filed on Apr. 11, 2001.

(51) Int. Cl.
*G06Q 10/00* (2006.01)
(52) U.S. Cl. .................. 705/4; 705/2; 705/3; 600/300; 600/301
(58) Field of Classification Search .................. 705/2–4; 600/300–301
See application file for complete search history.

(56) References Cited

U.S. PATENT DOCUMENTS 6,434,530 B1 * 8/2002 Sloane et al. .................. 705/1

2001/0032134 A1 * 10/2001 Hardesty ...................... 705/14

OTHER PUBLICATIONS

United Healthcare's Prescription Drug Management Company Addes Three Blue Cross and Blue Shield Contracts, PR Newswire, Jul. 18, 1991, Dialog ID No. 01773461; Supplier 42227723.*
www.aishealth.com/ManagedCare/BluesNews/BLU_Drug_Utlilization_Blues.html (published on May 25, 2006).*
"Employers Can Control Prescription Drug Costs Through Innovative Plans" by Bernard Handel, published in Pension World, Apr. 1989, vol. 25, Issue 4, p. 14.*
"Whither Medicare?" published in Intelligencer Journal of Lancaster, PA, Mar. 5, 2001—p. A6.*
Income Tax Theories—The Laffer Curve—Who Pays How Much? http://bized.ac.uk/virtual/economy/policy/tools/income/inctaxth5.htm (1 p.); printed Apr. 8, 2002.
Basic Economic Theory Supply & Demand and the Laffer Curve http://home.rmci.net/cbolton/ECON.HTM (4 pp.); printed Apr. 8, 2002.

* cited by examiner

*Primary Examiner*—Vivek D Koppikar
(74) *Attorney, Agent, or Firm*—The Webb Law Firm

(57) ABSTRACT

A method for determining an optimal sharing mix in a shared savings prescription plan, the method includes identifying a first drug group and a second drug group, wherein the first drug group and the second drug group are formulary equivalents of each other and each include one or more prescriptions, determining a total cost to the first entity for the first drug group and an estimated total cost to the first entity for the second drug group, determining a savings rate associated with utilizing the second drug group versus the first drug group, determining a distribution amount as a function of the savings rate and the total cost to the first entity for the first drug group, and distributing the distribution amount to at least one of a first entity, a second entity, and a third entity based upon one or more predetermined percentages.

21 Claims, 6 Drawing Sheets

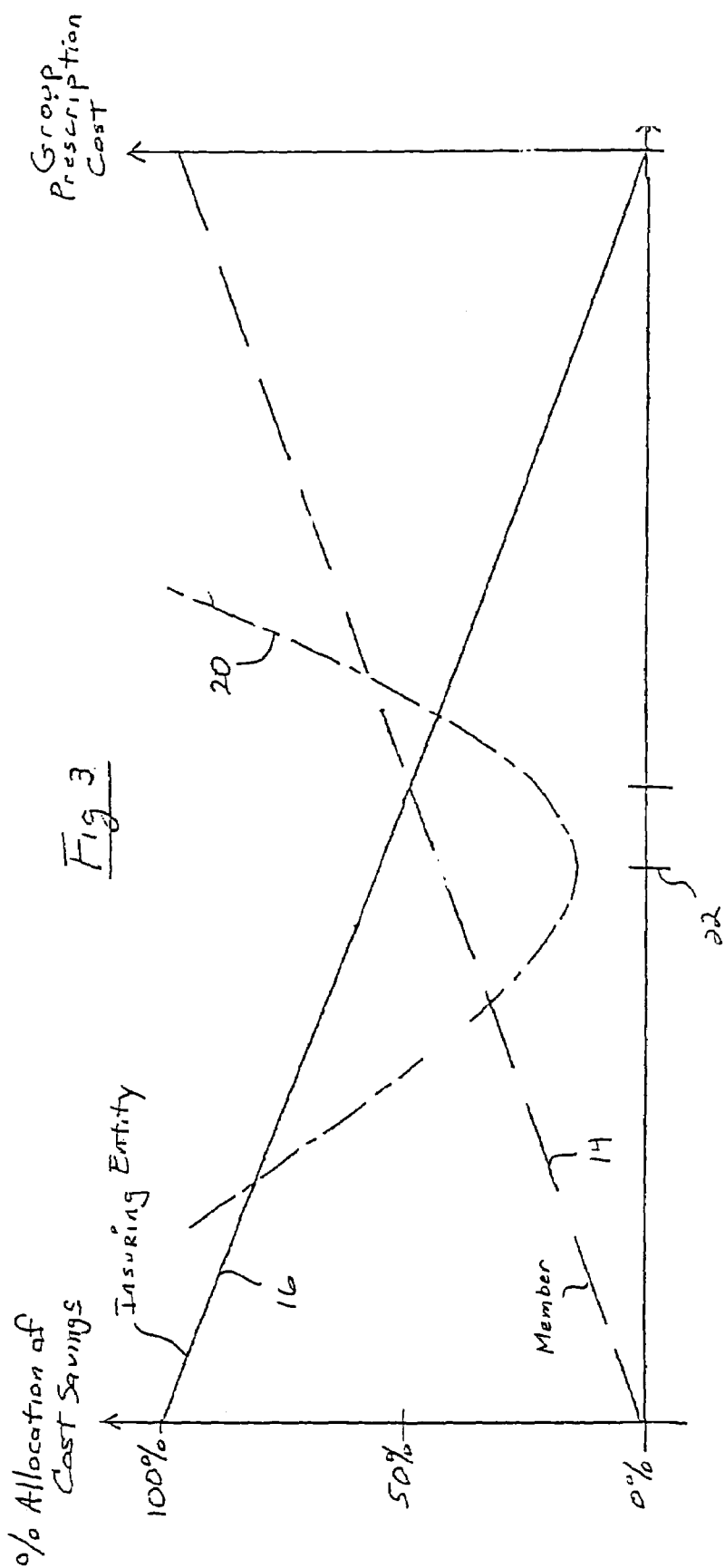

| SUMMARY DATA | | | | | | |
|---|---|---|---|---|---|---|
| DRUG NAME | THERAPEUTIC CLASS | # of Rxs | MEMBER PAID | CO-PAY/Rx | PLAN PAID | DBC |
| 1 OXYCONTIN 80 MG TABLET SA | "ANALGESICS - NARCOTIC" | 6 | $90.00 | $15.00 | $3,712.66 | $3,802.66 |
| 2 PREVACID 30 MG CAPSULE DR | "ULCER DRUGS" | 14 | $410.00 | $29.29 | $3,133.38 | $3,543.38 |
| 3 LIPITOR 10MG TABLET | "ANTIHYPERLIPIDEMIC" | 22 | $770.00 | $35.00 | $2,644.19 | $3,414.19 |
| 4 OXYCONTIN 40MG TABLET SA | "ANALGESICS - NARCOTIC" | 11 | $165.00 | $15.00 | $2,759.37 | $2,924.37 |
| 5 LIPITOR 20MG TABLET | "ANTIHYPERLIPIDEMIC" | 12 | $400.00 | $33.33 | $2,297.32 | $2,697.32 |
| 6 ACTIQ 400MCG LOZENGE | "ANALGESICS - NARCOTIC" | 3 | $45.00 | $15.00 | $2,232.00 | $2,277.00 |
| 7 CLARITIN 10MG TABLE | "ANTIHISTAMINES" | 16 | $380.00 | $23.75 | $1,887.23 | $2,267.23 |
| 8 PRAVACHOL 40MG TABLET | "ANTIHYPERLIPIDEMIC" | 8 | $260.00 | $32.50 | $1,959.78 | $2,219.78 |
| 9 NEXIUM 40MG CAPSULE | "ULCER DRUGS" | 6 | $210.00 | $35.00 | $1,621.07 | $1,831.07 |
| 10 LIPITOR 40MG TABLET | "ANTIHYPERLIPIDEMIC" | 4 | $140.00 | $35.00 | $1,122.54 | $1,262.54 |
| 11 ZOLOFT 100MG TABLET | "ANTIDEPRESSANTS" | 7 | $205.00 | $29.29 | $1,037.11 | $1,242.11 |
| 12 ZYRTEC 10MG TABLET | "ANTIHISTAMINES" | 15 | $325.00 | $21.67 | $912.00 | $1,237.00 |
| 13 PREVACID 15MG CAPSULE DR | "ULCER DRUGS" | 3 | $105.00 | $35.00 | $1,106.96 | $1,211.96 |
| 14 IMITREX 50MG TABLET | "MIGRANE PRODUCTS" | 6 | $90.00 | $15.00 | $1,088.67 | $1,178.67 |
| 15 AVANDIA 4MG TABLET | "ANTIDIABETIC" | 3 | $105.00 | $35.00 | $1,048.58 | $1,153.58 |
| 16 PRAVACHOL 20MG TABLET | "ANTIHYPERLIPIDEMIC" | 6 | $210.00 | $35.00 | $892.64 | $1,102.64 |
| 17 NORVASC 5MGTABLET | "CALCIUM BLOCKERS" | 11 | $385.00 | $35.00 | $707.09 | $1,092.09 |
| 18 PAXIL 20MG TABLET | "ANTIDEPRESSANTS" | 7 | $185.00 | $26.43 | $881.77 | $1,066.77 |
| 19 NORVASC 10MG TABLET | "CALCIUM BLOCKERS" | 7 | $245.00 | $35.00 | $809.83 | $1,054.83 |
| 20 ZOLOFT 50MG TABLET | "ANTIDEPRESSANTS" | 10 | $210.00 | $21.00 | $834.15 | $1,044.15 |
| 21 TRICOR 160MG TABLET | "ANTIHYPERLIPIDEMIC" | 6 | $190.00 | $31.67 | $790.62 | $980.62 |
| 22 PROAMATINE 5MG TABLET | "PRESSORS" | 3 | $45.00 | $15.00 | $931.32 | $976.32 |
| 23 ZOFRAN 4MG TABLET | "ANTIEMETICS" | 2 | $30.00 | $15.00 | $930.28 | $960.28 |
| 24 ASACOL 400MG TABLET EC | "MISC. GI" | 2 | $70.00 | $35.00 | $843.53 | $913.53 |
| 25 AUGEMENTIN 875-125 TABLET | "PENICILLINS" | 9 | $135.00 | $15.00 | $768.72 | $903.72 |
| TOTALS FOR TOP 25 | Q3 2002 | 199 | $5,405.00 | | $36,952.81 | $42,357.81 |
| TOTALS FOR TOP 25 | ANNUAL | 796 | $21,620.00 | | $147,811.24 | $169,431.24 |

1st DRUG GROUP

| DRUG NAME | PILL SPLIT | DOSE (MG) | TIMES / DAY | ESTIMATED SAVINGS % RETAIL / RETAIL | ESTIMATED SAVINGS AMT. NET / RETAIL | ESTIMATED DBC |
|---|---|---|---|---|---|---|
| 1 OXYCODONE-GENERIC | no | FOUR 5 * | 4 | 75% | $3,002.10 | $800.56 |
| 2 PROTONIX | no | 40 | 1 | 20% | $745.97 | $2,797.41 |
| 3 LIPITOR | yes | 40 | 1 | 46% | $1,653.19 | $1,761.00 |
| 4 OXYCODONE-GENERIC | no | 5 | 3 | 65% | $2,000.88 | $923.49 |
| 5 LIPITOR | yes | 20 | 1 | 27% | $766.61 | $1,930.71 |
| 6 NOT AVAILABLE | no | | | | $0.00 | $2,277.00 |
| 7 ZYRTEC | no | 10 | 1 | 26% | $620.51 | $1,646.72 |
| 8 LIPITOR 40 MG | no | 40 | 4 | 58% | $1,355.23 | $864.55 |
| 9 PREVACID | no | 30 | 1 | 2% | $38.55 | $1,792.52 |
| 10 LIPITOR | no | 80 | 1 | 50% | $664.49 | $598.05 |
| 11 CELEXA 200 MG | no | 40 | 1 | 51% | $666.82 | $575.29 |
| 12 CHLORPHENIRAMINE-GENERIC | yes | 12 | 2 | 89% | $1,158.87 | $78.13 |
| 13 PROTONIX | no | 40 | 1 | 20% | $255.15 | $956.81 |
| 14 MIGRANAL | no | 0.5 | 1 | 91% | $1,129.04 | $49.63 |
| 15 NOT AVAILABLE | no | | | | $0.00 | $1,153.58 |
| 16 LOVASTATIN-GENERIC | no | 20 | 1 | 53% | $615.16 | $487.48 |
| 17 NORVASC 10 MG | yes | 10 | 1 | 23% | $264.40 | $827.69 |
| 18 FLUOEXTINE-GENERIC | no | 20 | 1 | 43% | $482.85 | $583.92 |
| 19 SULAR | no | 30 | 2 | 49% | $544.07 | $510.76 |
| 20 FLUOEXTINE-GENERIC | no | 20 | 1 | 37% | $406.67 | $637.48 |
| 21 GEMFIBROZIL-GENERIC | no | 600 | 2 | 78% | $805.14 | $175.48 |
| 22 NOT AVAILABLE | no | | | | $0.00 | $976.32 |
| 23 NOT AVAILABLE | no | | | | $0.00 | $960.28 |
| 24 NOT AVAILABLE | no | | | | $0.00 | $913.53 |
| 25 NOT AVAILABLE | no | | | | $0.00 | $903.72 |
| | | | | | $17,175.71 | $25,182.10 |
| | | | | | 41% | |

* DISPENSING 4 TABLETS FROM A 5 TABLET PACKAGE

| | 2nd DRUG GROUP 69 | | | | | ESTIMATED SAVINGS % RETAIL/RETAIL 71b | ESTIMATED SAVINGS AMT. NET/RETAIL 72b | ESTIMATED DBC 73b |
|---|---|---|---|---|---|---|---|---|
| 70 → | DRUG NAME 69a | PILL SPLIT 69b | DOSE (MG) | TIMES/DAY | | | | |
| 1 | SAME AS 1ST DRUG GROUP | no | FOUR 5* | 4 | 75% | $3,002.10 | $800.56 |
| 2 | RANTIDINE-GENERIC | no | 150 | 1 | 90% | $3,356.89 | $186.49 |
| 3 | SAME AS 1ST DRUG GROUP | yes | 40 | 1 | 46% | $1,653.19 | $1,761.00 |
| 4 | SAME AS 1ST DRUG GROUP | no | 5 | 3 | 65% | $2,000.88 | $923.49 |
| 5 | SAME AS 1ST DRUG GROUP | yes | 20 | 1 | 27% | $766.61 | $1,930.71 |
| 6 | NOT AVAILABLE | no | | | | $0.00 | $2,277.00 |
| 7 | CHLORPHENIRAMINE-GENERIC | no | 12 | 2 | 92% | $2,195.63 | $71.60 |
| 8 | SAME AS 1ST DRUG GROUP | yes | 80 | 1 | 79% | $1,845.92 | $373.86 |
| 9 | RANTIDINE-GENERIC | no | 150 | 2 | 91% | $1,753.97 | $77.10 |
| 10 | SAME AS 1ST DRUG GROUP | no | 80 | 1 | 50% | $664.49 | $598.05 |
| 11 | SAME AS 1ST DRUG GROUP | yes | 40 | 1 | 51% | $666.82 | $575.29 |
| 12 | SAME AS 1ST DRUG GROUP | no | 12 | 2 | 89% | $1,158.87 | $78.13 |
| 13 | RANTIDINE-GENERIC | no | 150 | 2 | 90% | $1,148.17 | $63.79 |
| 14 | ASPRIN + METOCLOPRAMIDE-GENERIC | no | 900 + 10 | 1 | 100% | $1,237.23 | -$58.56 |
| 15 | NOT AVAILABLE | no | | | | $0.00 | $1,153.58 |
| 16 | LIPITOR | yes | 10 | 1 | 59% | $684.80 | $417.84 |
| 17 | SAME AS 1ST DRUG GROUP | yes | 10 | 1 | 23% | $264.40 | $827.69 |
| 18 | CELEXA | yes | 40 | 1 | 56% | $628.83 | $437.94 |
| 19 | SAME AS 1ST DRUG GROUP | no | 30 | 2 | 49% | $544.07 | $510.76 |
| 20 | CELEXA | yes | 40 | 1 | 52% | $571.53 | $472.62 |
| 21 | SAME AS 1ST DRUG GROUP | no | 600 | 2 | 78% | $805.14 | $175.40 |
| 22 | NOT AVAILABLE | no | | | | $0.00 | $976.32 |
| 23 | NOT AVAILABLE | no | | | | $0.00 | $960.28 |
| 24 | NOT AVAILABLE | no | | | | $0.00 | $913.53 |
| 25 | NOT AVAILABLE | no | | | | $0.00 | $903.72 |
| | | | | | | $24,949.56 | $17,408.25 |
| | | | | | | 59% | |

* DISPENSING 4 TABLETS FROM A 5 TABLET PACKAGE

METHOD AND APPARATUS FOR DETERMINING AN OPTIMAL SHARING MIX IN A SHARED PRESCRIPTION SAVINGS PLAN

CROSS REFERENCE TO RELATED APPLICATION

This application is a continuation-in-part application of U.S. patent application Ser. No. 10/121,472, filed Apr. 11, 2002, and entitled "Method of Distributing Cost Savings to Participants in a Prescription Drug Distribution Chain", which claims priority from U.S. Provisional Patent Application No. 60/283,000, filed Apr. 11, 2001, the contents of which are hereby incorporated herein by reference.

BACKGROUND OF THE INVENTION

1. Field of the Invention

The present invention is directed to a method and apparatus for determining an optimal sharing mix in a shared prescription savings plan utilizing various drug groups.

2. Description of Related Art

Heretofore, except for multi-tiered punitive co-payment structures, there has been little or no financial incentive for an insured member to request the prescription of a generic drug by their physician, especially a member who has all or part of their insurance premiums paid by a third party.

It is, therefore, desirable to overcome the above problem and others by providing a method for inducing members to request prescription of a generic drug versus a brand name drug. It is also desirable to provide an optimal sharing mix of a savings amount among participants in a shared savings prescription plan. It is also desirable to provide a thorough and comprehensive overview of an insuring entity's drug utilization characteristics for various drug groups.

Still other desirable features of the invention will become apparent to those of ordinary skill in the art upon reading and understanding the following detailed description.

SUMMARY OF THE INVENTION

Accordingly, I have invented a method of distributing savings related to the distribution of a prescription drug. The method includes identifying participants of a plan that participate in the distribution of a prescription drug or the payment for the distribution to one of the participants. A determination is made that the one participant acquired a first form of a prescription drug for which a second, more costly form exists. A cost difference between the first and second forms of this prescription drug is determined and this cost difference is allocated to at least two of the participants.

The one participant includes a member. The other participants can include an entity insuring the member for all or part of the cost of the prescription drug, a physician prescribing the prescription drug to the member, a pharmaceutical entity which causes the prescription drug to be dispensed to the member, a pharmaceutical benefits managing entity, and/or a method facilitating entity.

The method can further include distributing to at least one participant the cost difference allocated thereto. This distribution can include distributing to the member the cost difference allocated to the member and/or distributing to a third party entity designated by the physician the cost difference allotted to the physician.

The cost difference distributed to the member can be in the form of a credit to be applied toward the acquisition of additional quantities of the same or another prescription drug.

The method can further include distributing to at least one of the pharmaceutical entity, the benefits managing entity, and the method facilitating entity the cost difference allotted thereto.

Preferably, each participant is allotted a predetermined percentage of the cost difference, where each predetermined percentage is either the same or different than any of the other predetermined percentages.

I have also invented a method of distributing cost savings realized from the distribution of a prescription drug. The method includes enrolling participants at different levels of a prescription drug distribution and payment chain in a plan for distributing cost savings realized from the selection of a generic form of a prescription drug over a brand name form of the prescription drug. Next, a determination is made that a member participant received a generic form of a prescription drug for which a brand name form exists. A cost difference is determined between the generic and brand name forms of the prescription drug and a percentage of the cost difference is allocated to one or more of the enrolled participants.

The cost difference is allocated to one or more non-member participants based on each non-member participant participating in the member participant receiving the generic form of the prescription drug and/or a payment related to the member participant receiving the generic form of the prescription drug.

The method can also include distributing to at least one enrolled participant the cost difference allotted to the participant.

Furthermore, I have invented a method of prescription drug cost savings distribution. The method includes enrolling in a plan for distributing cost savings realized from selecting a generic form of a prescription drug over a brand name form of the prescription drug. The generic form of the prescription drug is then selected and at least a portion of a difference between the cost of the generic form of the prescription drug and the cost of the brand name form of the prescription drug is received. The portion of the difference can be received in the form of cash, a check, or a credit.

The method can also include distributing plural portions of the cost difference to enrollees of the plan based on each enrollee participating in the receipt of the generic form of the prescription drug and/or a payment related to the receipt of the first form of the prescription drug.

Lastly, I have invented a method for determining an optimal sharing mix in a shared savings prescription plan. The method comprises the steps of identifying an insuring entity, one or more members of the insuring entity, and a plan facilitator responsible for facilitating the shared savings prescription plan for the insuring entity. Additionally, the total drug benefit cost for at least a first drug group and a second drug group in the shared savings prescription plan is determined. Each drug group includes one or more prescriptions. Then, a savings rate incurred by having the one or more members utilizing the second drug group as opposed to utilizing the first drug group is determined. The savings rate is applied to the total drug benefit cost of the first drug group to determine an estimated distribution amount. The estimated distribution amount represents an average savings for the one or more prescriptions when the one or more members utilize the second drug group as opposed to the first drug group. A commission rate, an insuring entity share rate, and a member share rate are applied to the estimated distribution amount to determine a plan facilitator amount, an insuring entity amount, and a member amount. These amounts are then distributed to the participants of the shared savings prescription plan.

These and other advantages of the present invention will be understood from the description of the desirable embodiments, taken with the accompanying drawings, wherein like reference numbers represent like elements throughout.

BRIEF DESCRIPTION OF THE DRAWINGS

FIG. 3 is a graph of percent allocation of cost savings having superimposed thereon an inverse Laffer Curve of group prescription cost;

FIG. 4a is a diagram of historical summary data comprising individual prescriptions available in a shared savings prescription plan;

FIG. 4b is a diagram of a "$1^{st}$ Drug Group" comprising individual prescriptions available in the shared savings prescription plan; and FIG. 4c is a diagram of a "$2^{nd}$ Drug Group" comprising individual prescriptions available in the shared savings prescription plan.

DETAILED DESCRIPTION OF THE INVENTION

The present invention will now be described with reference to the accompanying figures. As used herein, the phrases generic form of a prescription drug, generic drug, generic prescription drug, and the like, are intended to include not only a generic drug that is a formulary equivalent to a brand name drug but also to an alternative drug that has a lower cost than the brand name drug. Accordingly, the phrases generic drug, generic prescription drug, generic form of a prescription drug, and the like, are intended to convey the concept of one form of a prescription drug that is less costly than another form of a formulary equivalent prescription drug.

Figure 1:
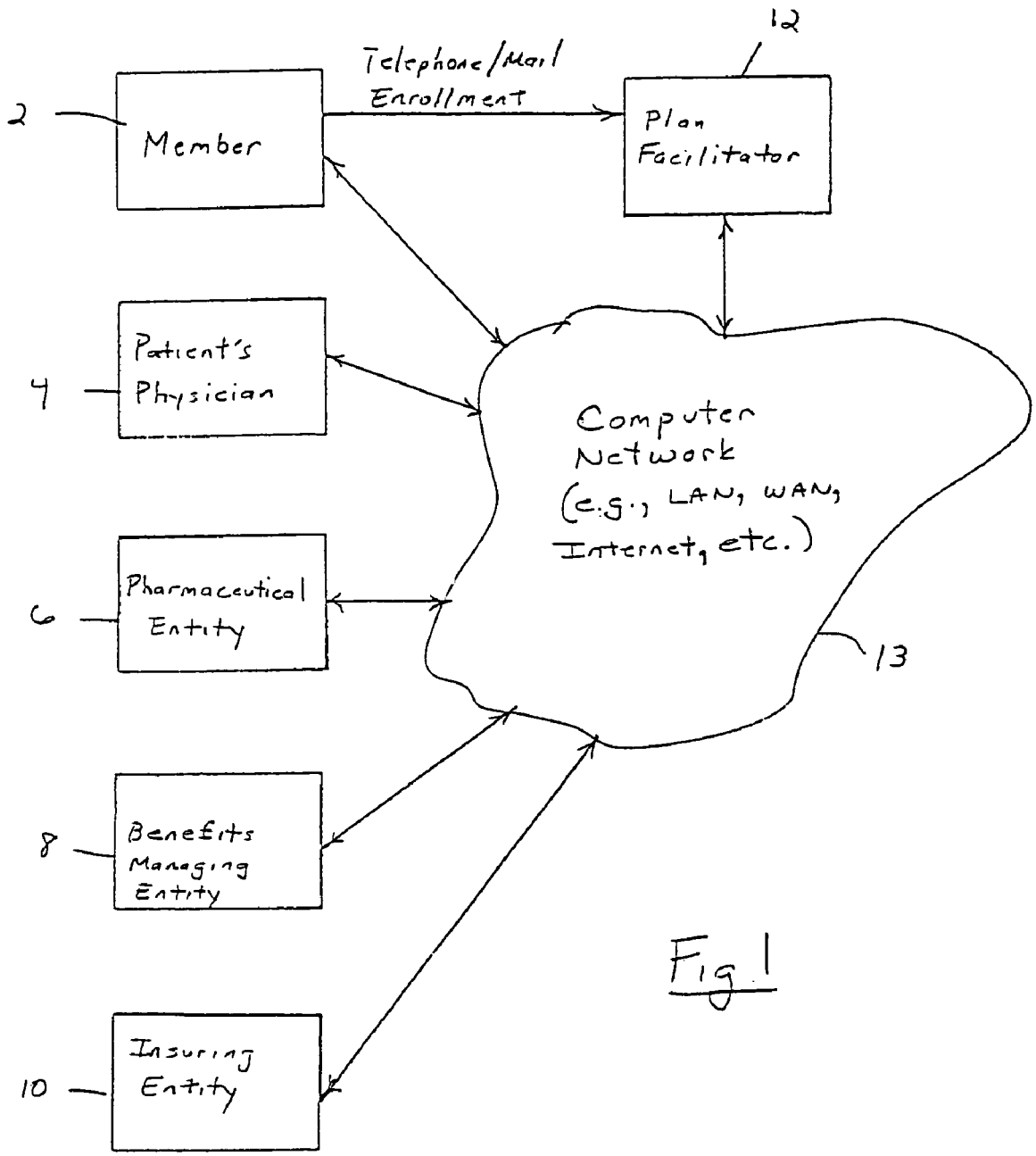
FIG. 1 is a block diagram of participants of a plan for sharing the cost difference between generic and brand name pharmaceuticals communicatively connected together via a computer network.

With reference to FIG. 1, in connection with the distribution of a prescription drug to an insured member 2 by a pharmaceutical entity 6 based on a prescription ordered for member 2 by physician 4, there is often one or more other entities that participate in the distribution and/or have a financial interest in the distribution. One such entity includes an insuring entity 10 that may be contractually obligated to pay all or part of the costs of the prescription drug dispensed to member 2. Another entity may include a benefits managing entity 8 that works with pharmaceutical entity 6 on behalf of insuring entity 10. For example, at a point of sale of the prescription drug to member 2, pharmaceutical entity 6 contacts benefits managing entity 8 to ensure that member 2 has active insurance coverage, the extent to which this insurance coverage covers the cost of the prescription drug being dispensed to member 2, and any applicable discounts for the prescription drug negotiated between pharmaceutical entity 6 and insuring entity 10. Based on this information, benefits managing entity 8 authorizes reimbursement to pharmaceutical entity 6 on behalf of insuring entity 10 for the insured cost of the prescription drug being dispensed to member 2. Pharmaceutical entity 6 then charges member 2 any difference between this insured cost and the point of sale cost to member 2. Absent benefits managing entity 8, pharmaceutical entity 6 obtains this information directly from insuring entity 10.

The present invention will now be described with reference to entities 2-10 being enrolled in a plan which is administered by a plan facilitator 12. However, other participants, such as drug companies, Internet sites, and the like, that participate in the dispensing of the prescription drug and/or have a financial interest in the dispensing of the prescription drug may also be plan participants. For purposes of illustration, exemplary cost savings realized by the dispensing of a generic prescription drug over a brand name, a formulary equivalent prescription drug will be described. In addition, a percent allocation and distribution of the savings in accordance with the present invention will also be described by way of example. However, these examples are not to be construed as limiting the invention in any manner.

Initially, participants 2-10 at different levels of a prescription drug distribution and payment chain are enrolled in a plan for distributing cost savings realized from the dispensing of a generic form of a prescription drug over a brand name form of the prescription drug. Preferably, physician 4, pharmaceutical entity 6, and insuring entity 10 are initially enrolled in the plan. If a benefits managing entity 8 is utilized by insuring entity 10, benefits managing entity 8 is also enrolled as a participant in the plan. Thereafter, member 2 can be enrolled in the plan at a suitable time. However, this order of enrollment is not to be construed as limiting the invention.

Since an order or prescription for a prescription drug originates with physician 4, physician 4 controls whether member 2 is prescribed a generic drug versus a brand name drug. To this end, when prescribing a prescription drug for member 2, if physician 4 believes a generic drug will work as effectively as a brand name drug, physician 4 either unilaterally writes the prescription for a generic drug or can consult with member 2 as to the member's 2 preference for a generic drug versus a brand name drug. This consultation may include physician 4 advising member 2 that they can participate in any cost savings realized by insuring entity 10 in response to member 2 agreeing to permit physician 4 to prescribe, and physician 4 prescribing a generic drug versus a formulary equivalent brand name drug.

As a result of prescribing a generic drug over a brand name drug, insuring entity 10 allocates a percentage of any cost savings realized by insuring entity 10 as a result of this selection to member 2 and physician 4. Since physician 4 is often precluded from accepting compensation for prescribing certain prescription drugs, when the time comes to pay the percentage of the cost savings allocated to physician 4, this percentage is paid to a designee, e.g., a medical institution or charity, of the doctor's choosing.

To facilitate member 2 joining the plan, brochures and other like information can be provided to physician 4 for distribution to member 2. These brochures and other like information can be provided by insuring entity 10 or any other entity, such as a generic drug company, that stands to profit from member 2 receiving a generic drug versus a comparable brand name drug.

If member 2 elects to participate in the plan, member 2 and other plan participants preferably enroll in the plan with plan facilitator 12 via a computer network 13, such as the Internet. However, this is not to be construed as limiting the invention since participants can enroll in the plan telephonically and/or by mail. Once enrolled in the plan, computer network 13 is utilized by the plan participants to facilitate the plan. However, this is not to be construed as limiting the invention since the plan participants can also or alternatively facilitate the plan telephonically and/or by mail. For example, member 2 can enroll in the plan with plan facilitator 12 via computer network 13, by calling a telephone number hosted by plan facilitator 12, by mailing a registration form to plan facilitator 12, or by some combination thereof. To encourage members to enroll via computer network 13, the brochures or other like materials promoting the plan can explain that member 2 can receive a larger share of realized cost savings by registering via computer network 13, e.g., online via an Internet webpage, versus registering via telephone or by mail.

At any time during the member's participation in the plan, member 2 can elect to receive his percentage of the cost savings realized by insuring entity 10 in the form of a check, an insurance premium reduction, a defined benefit credit, and/or a donation to a designated charity of the member's choosing.

Once member 2 has completed his enrollment, insuring entity 10, or benefits managing entity 8 on behalf of insuring entity 10, verifies the insurance data of member 2 and member registration is confirmed via computer network 13 and/or by written notice. Thereafter, member 2 would be eligible to receive a percentage of the cost savings realized by insuring entity 10 when member 2 is dispensed a generic drug over a brand name drug that is more costly than the generic drug.

Insuring entity 10 participates in the plan by completing a registration agreement with plan facilitator 12. The registration agreement contractually obligates insuring entity 10 to pay predetermined percentages of the realized cost savings between a generic drug and a comparable brand name drug directly to a selected designee of physician 4, member 2, plan facilitator 12, pharmaceutical entity 6, and/or benefits managing entity 8.

The incentive for insuring entity 10 to participate in the plan is the economic benefit that flows to insuring entity 10 when a member is dispensed a generic drug over a more costly brand name drug. Specifically, insuring entities generally receive sufficient funds to pay all or most of the cost of prescription drugs from insurance premiums received from members and/or third parties on behalf of members, e.g., employers. If insuring entity 10 pays less for a prescription because a generic drug with identical therapeutic properties to an available brand name drug is prescribed by physician 4, either unilaterally or at the request of member 2, insuring entity 10 will have excess funds available to it as a result of this selection.

These excess funds can be used to increase profits of the insuring entity 10 and/or reduce overall insurance premiums. However, in accordance with the present invention, a significant financial incentive is provided to member 2 when insuring entity 10 shares the cost savings by allocating and distributing to member 2 a percentage of the savings in the form a check, premium reduction, benefit credit, and/or donation to member's 2 selected charity. The percentage of the cost savings allocated to member 2 must be sufficient to encourage member 2 to enter the plan since most members would not be motivated to benefit insuring entity 10 unless member 2 receives a benefit as well. The present invention enables significant financial benefits to be realized by member 2 by sharing cost savings realized by insuring entity 10 when member 2 is dispensed a generic drug versus a brand name drug.

In addition to member 2, physician 4, insuring entity 10, and plan facilitator 12, additional participants in the plan can include pharmaceutical entity 6 and benefits managing entity 8. Specifically, often times, prescriptions are written in a manner whereupon a pharmacist of pharmaceutical entity 6 dispensing the prescription has the option of substituting a generic drug for a brand name drug if member 2 consents to the substitution. To encourage pharmaceutical entity 6 to promote the use of generic drugs, pharmaceutical entity 6 can also be allotted and distributed a portion of the cost savings realized by insuring entity 10 from the dispensing of a generic drug over a brand name drug. To be eligible to receive the portion of the cost savings, pharmaceutical entity 6 enrolls in the plan with plan facilitator 12 whereupon pharmaceutical entity 6 agrees to promote the plan to its customers. This promotion by pharmaceutical entity 6 can either be passive promotion, e.g., signs, brochures, etc., or active promotion, e.g., where the pharmacist advises the member of the plan.

Benefits managing entity 8 can also participate in the plan by agreeing to promote the plan with pharmaceutical entities 6 with whom it does business. To this end, once enrolled in the plan, benefits managing entity 8 can receive a portion of the cost savings realized by insuring entity 10 when member 2 is dispensed a generic drug over a brand name drug.

For the purpose of distributing the percentages of the cost savings appropriately, a computer (not shown) of plan facilitator 12 can be programmed to record which participants 2-10 enrolled in the plan participated in the dispensing of a generic drug to member 2 and/or payment for the dispensing. For example, in one exemplary transaction, physician 4 prescribes a generic drug to be dispensed to member 2 by pharmaceutical entity 6. When member 2 arrives at pharmaceutical entity 6 to receive his prescription, pharmaceutical entity 6 confirms with insuring entity 10 that pharmaceutical entity 6 will receive all or an agreed upon portion of the cost of pharmaceutical entity 6 dispensing the generic drug to member 2. Thereafter, pharmaceutical entity 6 dispenses the generic drug to member 2 after receiving any required co-payment from member 2. In this transaction, the participants included member 2, physician 4, pharmaceutical entity 6, and insuring entity 10. Data regarding the participants in this transaction can be provided to plan facilitator 12 by any one of participants 2, 4, 6, or 10. However, it is envisioned that pharmaceutical entity 6 will provide data regarding participants in this transaction to plan facilitator 12 since pharmaceutical entity 6 typically creates a complete record of the transaction including the identity of member 2, the identity of physician 4, and the identity of insuring entity 10 that makes payments to pharmaceutical entity 6 on behalf of member 2. To this end, it is envisioned that a computer or computer system of pharmaceutical entity 6 can be programmed to interface with a computer or computer system of insuring entity 10 and plan facilitator 12 via computer network 13 so that data regarding each eligible transaction under the plan is available to insuring entity 10 and plan facilitator 12.

In another exemplary transaction, physician 4 prescribes a generic drug to be dispensed to member 2 by pharmaceutical entity 6. When member 2 arrives at pharmaceutical entity 6 to receive this prescription, pharmaceutical entity 6 confirms with benefits managing entity 8 that pharmaceutical entity 6 will receive all or an agreed portion of the cost of pharmaceutical entity 6 dispensing the generic drug to member 2 from insuring entity 10. Thereafter, pharmaceutical entity 6 dispenses the generic drug to member 2 after receiving any required co-payment from member 2. In this transaction, the participants included member 2, physician 4, pharmaceutical entity 6, benefits managing entity 8, and insuring entity 10. Data regarding the participants in this transaction is provided to plan facilitator 12 by any one of participants 2-10, e.g., pharmaceutical entity 6.

Plan facilitator 12 organizes the plan among the participants and facilitates the plan's operations. For example, plan facilitator 12 preferably manages an Internet website used for online registration and manages the exchange of forms with members not registering via the Internet website. Plan facilitator 12 can also develop or have developed the software that facilitates the plan as well as manage the software once implemented. Plan facilitator 12 can further manage the distribution of cost savings realized by insuring entity 10 to other participants in the plan. To this end, it is envisioned that whenever a generic drug is dispensed over a brand name drug, insuring entity 10 will withdraw its percent allocation from the cost savings and forward the reminder to plan facilitator 12 for distribution. After receipt of these funds, plan facilitator 12 withholds its percent allocation of the cost savings and, at an appropriate time, distributes the reminder to other qualified participants.

Figure 2:
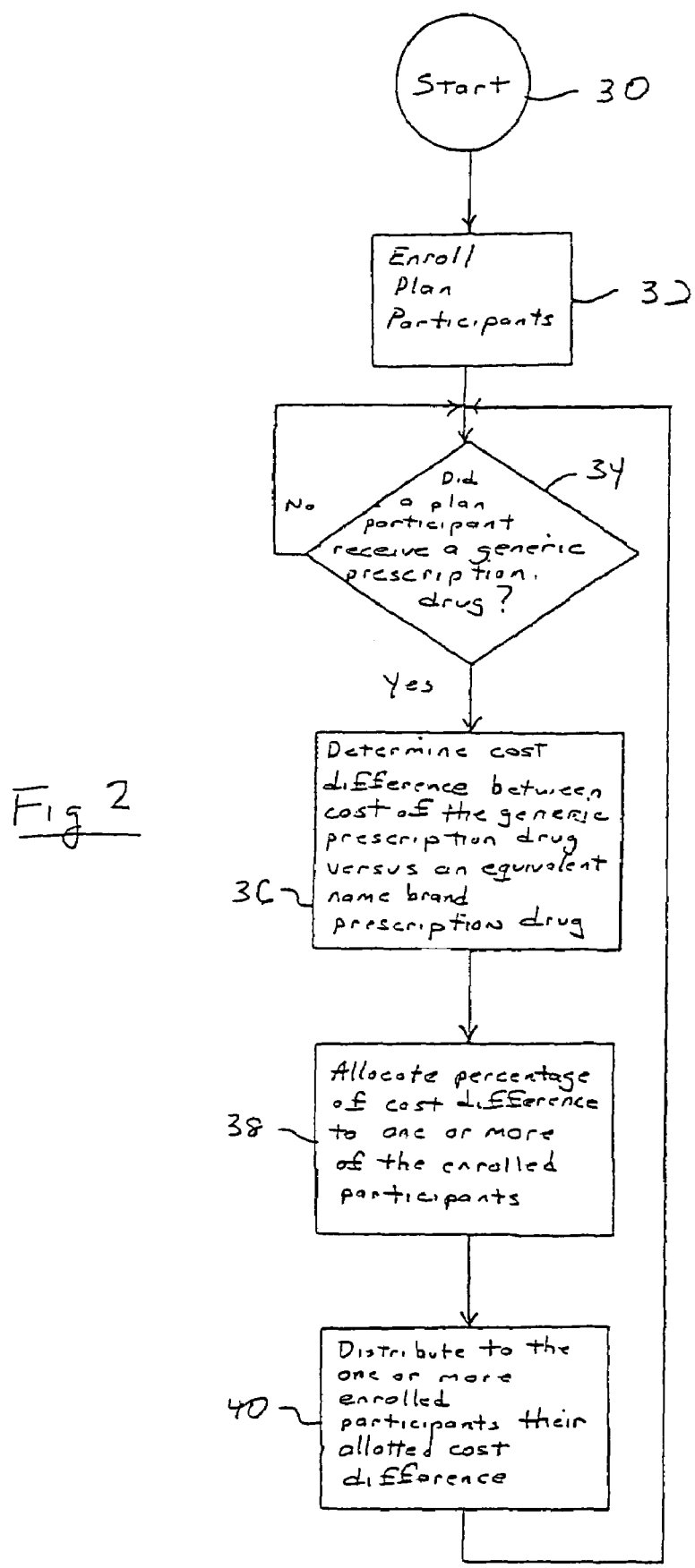
FIG. 2 is a flow diagram of a method for sharing the cost difference between generic and brand name pharmaceuticals in accordance with the present invention.

With reference to FIG. 2, the basic steps of the plan will now be described. Initially, when a decision is made to initiate the plan, the plan is advanced from step 30 to step 32 where plan participants enroll in the plan. Thereafter, the plan advances to step 34 where a determination is made whether a plan participant received a generic prescription drug. If not, the plan loops on this step 34 until a plan participant receives a generic prescription drug. However, if a plan participant receives a generic prescription drug, the plan advances to step 36. In step 36, a cost difference between the cost of the generic drug versus an equivalent brand name drug is determined. In step 38, various percentages of this cost difference are allocated to two or more of the enrolled participants. Preferably, each participant receiving a percentage of the cost difference participates in the dispensing of the generic drug and/or has a financial interest in the distribution of the generic drug versus an equivalent brand name drug. However, this is not to be construed as limiting the invention. Lastly, in step 40, the allotted cost difference is distributed to one or more enrolled participants or their designees. Steps 34-40 are then repeated as necessary for each plan participant receiving a generic prescription drug.

In FIG. 2, plan participants can be enrolled at anytime. Moreover, in the event there is no cost difference determined in step 36, no allocation or distribution of this cost difference in steps 38 and 40 is made.

As can be seen, one aspect of the present invention provides a method for inducing members to request the prescription of generic drugs versus brand name drugs by enabling the member to share in any cost savings realized by the insuring entity from the selection.

The following Table 1 shows an exemplary allocation of cost savings realized by insuring entity 10 when member 2 is dispensed a generic drug over a brand name drug.

TABLE 1

| Participant | Cost Savings Share Rates |
| --- | --- |
| Member | 45% |
| Physician | 3% |
| Pharmaceutical Entity | 3% |
| Benefits Managing Entity | 4% |
| Insuring Entity | 30% |
| Plan Facilitator | 15% |

The participants and/or allocation of cost savings shown in the foregoing table are for the purpose of illustration and are not to be construed as limiting the invention.

With reference to FIG. 3, it can be theoretically determined by application of an inverse Laffer Curve to a percent allocation of cost savings between insuring entity 10 and member 2 where the allocation of cost savings will result in the lowest group prescription cost. For example, in FIG. 3, member curve 14 and insuring entity curve 16 illustrate the relationship of percent allocation of cost savings between member 2 and insuring entity 10. Specifically, increasing the percent allocation of cost savings to member 2 from 0 to 100% results in a decrease in the percent allocation of cost savings to insuring entity 10 from 100% to 0%. Utilizing economic theories underlying the Laffer Curve for determining the percent tax rate that will result in a maximum tax revenue, the inverse Laffer Curve 20 shown in FIG. 3 can be plotted for group prescription cost to determine where the optimum mix or lowest group cost 22 as a function of percent allocation between insuring entity 10 and member 2 occurs. In FIG. 3, the slope of curves 14 and 16 and the position of inverse Laffer Curve 20 can be adjusted based on percentages of the cost savings being allocated to other participants of the plan.

In practice, curves 14, 16, and 20 are determined from empirical data acquired from the percent of cost savings allocated to insuring entity 10 and member 2 at various points along the horizontal axis. The empirical data from these test simulations can then be utilized to empirically determine the shape and location of the inverse Laffer Curve 20. The graphs shown in FIG. 3 are for purposes of illustration only and are not to be construed as limiting the invention.

With reference to FIG. 4a, and with continuing reference to FIG. 1, to arrive at the empirical data, insuring entity 10 obtains from its pharmaceutical benefits managing entity 8 summary data 42 for, for example, the top twenty-five drugs paid for over a predetermined period of time, e.g., quarterly, annually, etc., for a drug plan. For simplicity of description, the summary data 42 will be described as being acquired over one quarter, i.e., three months, however, this is not to be construed as limiting the invention. Summary data 42 can include, but is not limited to, the following columns containing information concerning each drug: a drug name 44, a therapeutic class 46, a number of prescriptions 48, a member paid amount 50, a co-payment per prescription amount 52, a plan paid amount 54, and a drug benefit cost 56. Drug name 44 column includes the names of the top twenty-five drugs in the drug plan and their recommended dosage. Therapeutic class 46 column includes a classification of each drug in the drug plan. Number of prescriptions 48 column includes the number of prescriptions dispensed for each of the drugs in the drug plan. Member paid amount 50 column shows the total cost paid by all members in the drug plan for each of the drugs in the drug plan. Co-payment per prescription amount 52 column includes an average co-payment amount paid by members of the drug plan for each prescription for a particular drug. Thus, multiplying the co-payment per prescription amount 52 by the number of prescriptions 48 yields member paid amount 50. Plan paid amount 54 column includes, for each drug in the drug plan, the amount paid by insuring entity 10 for all prescriptions of that drug. Drug benefit cost (DBC) 56 column includes, for each drug in the drug plan, the sum of the member paid amount 50 and the plan paid amount 54. Summary data 42 provides useful information including, but not limited to, a total quarterly member paid amount 58, a total quarterly plan paid amount 59, and a total quarterly drug benefit cost 60. Total quarterly member paid amount 58 and total quarterly plan paid amount 59 are determined by summing the member paid amounts 50 and the plan paid amounts 54, respectively, for each drug in the drug plan. Total quarterly drug benefit cost 60 is determined by summing the total quarterly member paid amount 58 and the total quarterly plan paid amount 59. Additionally, summary data 42 may also provide a total annual member paid amount 62, a total annual plan paid amount 63, and a total annual drug benefit cost 64. These additional amounts reflect the costs associated with the drug plan for a year, i.e., four times the amount of each quarterly cost.

With reference to FIGS. 4b and 4c, and with continuing reference to FIG. 4a, the basic steps of determining an optimal sharing mix in a shared savings prescription plan will now be described. The method determines an average savings that would be realized if a less expensive drug plan, as opposed to the drug plan outlined in summary data 42, were to be utilized. More specifically, an average prescription savings for each member of the plan or for the entire plan can be determined.

Based on summary data 42, lower cost prescription alternatives are developed with attendant savings possible using various cost-saving techniques 66 and 69. These cost-saving techniques 66 and 69 include, but are not limited to, generic drugs 66a, 69a; pill splitting 66b, 69b; therapeutic substitution (not shown); disease management (not shown); and mail orders (not shown). In a desirable embodiment, the lower cost prescription alternatives are embodied in one or more formulary equivalent drug groups 68, 70 entitled "1$^{st}$ Drug Group" and "2$^{nd}$ Drug Group", respectively. For example, "1$^{st}$ Drug Group" 68 employs Oxycodone, a generic drug 66a, as an alternative to the more expensive name brand drug, Oxycontin, found in summary data 42. As a further example, the fifth drug in summary data 42 is Lipitor 20 mg tablet. The fifth drug in "1st Drug Group" 68 is also Lipitor, but the tablet size is 40 mg and it has pill splitting 66b associated with it. Thus, the dosage, i.e., 20 mg, remains the same regardless of whether summary data 42 or "1st Drug Group" 68 is selected, but member 2 is required to split a 40 mg tablet into two 20 mg portions if "1st Drug Group" is selected. As can be seen in "1st Drug Group" 68 and "2nd Drug Group" 70, each drug group may contain drugs similar and/or identical to those found in summary data 42, as there may not be a generic equivalent or other cost-saving technique 66 associated with a particular drug. It is to be understood that the present invention may include as many drug groups as there are lower cost prescription alternatives available.

An estimated savings percentage 71a and 71b is associated with each cost-saving technique 66 in drug groups 68 and 70, respectively. Estimated savings percentage 71a and 71b are each multiplied with drug benefit cost 56 for a particular drug from summary data 42, optionally taking into account a retail discount. This results in a drug estimated savings 72a and 72b for each drug in drug groups 68 and 70, respectively. For example, insuring entity 10 may receive an overall 5% retail discount for each drug in summary data 42, "1st Drug Group" 68, and "2nd Drug Group" 70. The drug benefit cost 56 for Oxycontin in summary data 42 is $3,802.66. The associated estimated savings percentage 71a for Oxycodone in "1st Drug Group" 68 is 75%. Thus, $3,802.66 is multiplied by 75% and is divided by 95% (100%-5% retail discount) to yield $3,002.10, or estimated savings amount 72a. Thus, $3,002.10 is saved by utilizing Oxycodone as opposed to Oxycontin. Subtracting estimated savings amount 72a and 72b from drug benefit cost 56 for a particular drug yields an estimated drug benefit cost 73a and an estimated drug benefit cost 73b, respectively. Furthermore, drug groups 68 and 70 include total estimated drug benefit costs 74a and 74b, respectively. The value of total estimated drug benefit costs 74a and 74b is derived by summing drug benefit costs 73a and 73b for each drug group 68 and 70, respectively. Total estimated drug benefit costs 74a and 74b may take into account estimated member co-payments. Furthermore, drug groups 68 and 70 include total estimated savings amounts 75a and 75b, respectively. Total estimated savings amounts 75a and 75b are derived by summing estimated savings amounts 72a and 72b for each drug in drug groups 68 and 70, respectively. In the desirable embodiment, estimated savings amounts 72a and 72b and total estimated savings amounts 75a and 75b are representative of gross savings, as opposed to net savings, in the shared savings prescription plan. Alternatively, total estimated savings amounts 75a and 75b may be derived by subtracting total estimated drug benefit costs 74a and 74b from the total quarterly drug benefit cost 60. Savings rates 76a and 76b can also be associated with each drug group 68 and 70 to indicate the percentage saved by utilizing either one of the drug groups 68 and 70, respectively, as opposed to utilizing the summary data 42.

For example, total quarterly drug benefit cost 60 incurred by utilizing summary data 42 is $42,357.81, whereas total estimated drug benefit cost 74a from "1st Drug Group" 68 is $25,182.10. Thus, the total estimated savings amount 75a for "1st Drug Group" 68 is calculated to be $17,175.71, i.e., $42,357.81-$25,182.10. Dividing the total estimated savings amount 75a, i.e., $17,175.71, by the total quarterly drug benefit cost 60, $42,357.81, yields savings rate 76a, which is 40.5491%. Therefore, savings rate 76a realized by utilizing "1st Drug Group" 68 is approximately 41%. This process can also be applied to "2nd Drug Group" 70 to determine savings rate 76b, which is approximately 59%.

The following Table 2 shows exemplary data for determining the optimal sharing mix in the shared savings prescription plan, wherein "1st Drug Group" 68 and "2nd Drug Group" 70 are utilized. It is to be understood that the estimated data shown for the "1st Drug Group" 68 and the "2nd Drug Group" 70 is used for illustrative purposes and is not to be construed as limiting the invention.

TABLE 2

|  | Summary Data | 1st Drug Group | 2nd Drug Group |
|---|---|---|---|
| Total Drug Benefit Cost | $ 42,357.81 | $ 25,182.10 | $ 17,408.25 |
| Estimated Savings Amt. | $ N/A | $ 17,175.71 | $ 24,949.56 |
| Saving Rate | 0% | 40.5491% | 58.9019% |
| Estimated Distribution Amt. | $ 0.00 | $ 17,175.71 | $ 24,949.56 |
| Compliance Rate | 30% | 70 | |
| Drug Group Probability | 0% | 40% | 60% |
| Distribution Amt. (having Compliance Rate and Drug Group Probability applied) | $ 0.00 | $ 4,809.20 | $ 10,478.82 |
| Plan Facilitator Amt. | $ 0.00 | $ 721.38 | $ 1,571.82 |
| Insuring Entity Amt. | $ 0.00 | $ 1,442.76 | $ 3,143.65 |
| Member Amt. | $ 0.00 | $ 2,164.14 | $ 4,715.47 |

The savings rate 76a may be combined with total quarterly drug benefit cost 60 to determine an estimated distribution amount, preferably in dollars, realized by utilizing the drugs in "1$^{st}$ Drug Group" 68 in the plan as opposed to the drugs provided in summary data 42. For example, the total quarterly drug benefit cost 60 is multiplied by savings rate 76a, i.e., 40.5491% to obtain an amount of $17,175.71 that represents the estimated per quarter distribution amount realized by utilizing "1$^{st}$ Drug Group" 68. Similarly, a different estimated distribution amount can be determined when utilizing "2$^{nd}$ Drug Group" 70 as opposed to "1$^{st}$ Drug Group" 68. The estimated distribution amount can be calculated for any predetermined period of time, e.g., three months, one year, etc.

The method also takes into account a compliance rate, as shown in Table 2. The compliance rate is an estimated percentage of members 2 who would participate in the shared savings prescription plan, regardless of whether each of members 2 utilizes "1$^{st}$ Drug Group" 68 or "2$^{nd}$ Drug Group" 70. Accordingly, the percentage of members 2 who would participate in the shared savings prescription plan may be less than 100%. For example, as illustrated in Table 2, 70% of all members 2 of insuring entity 10 may wish to enroll in the shared savings prescription plan, whereas the remaining 30% of members 2 may wish to continue to utilize the drug group specified in summary data 42. Thus, only 70% of all members 2 insured by insuring entity 10 would be eligible to receive any portion of the estimated distribution amount. Additionally, it is possible that of those members 2 participating in the shared savings prescription plan, some of members 2 wish to utilize "1$^{st}$ Drug Group" 68 while the other members wish to utilize "2$^{nd}$ Drug Group" 70. Members 2 may see more of an incentive to use one drug group over another drug group based upon the lower costs associated therewith and, hence, the increased estimated distribution amount realized. For example, of the 70% of all members 2 participating in the shared savings prescription plan, 40% may wish to utilize "1$^{st}$ Drug Group" 68, while 60% may wish to utilize "2$^{nd}$ Drug Group" 70. To this end, the method incorporates a "1$^{st}$ Drug Group" probability and a "2$^{nd}$ Drug Group" probability, representing a first and second proportion of members utilizing "1$^{st}$ Drug Group" 68 and "2$^{nd}$ Drug Group" 70, respectively. It is to be understood that consumer behavior models may be used to generate compliance estimates as well as the relative probability of drug group choice.

For example, the estimated distribution amount for the "1$^{st}$ Drug Group" 68 is $17,175.71. Since only 40% of the members 2 participating in the shared savings prescription plan utilize the "1$^{st}$ Drug Group" 68, the estimated distribution amount for the "1$^{st}$ Drug Group" 68 is multiplied by the compliance rate (70%) and the "1$^{st}$ Drug Group" probability (40%) to obtain an amount of $4,809.20. This amount is representative of a distribution amount having the compliance rate and the drug group probability applied to it. Similarly, the estimated distribution amount for the "2$^{nd}$ Drug Group" 70 is multiplied by the compliance rate (70%) and the "2$^{nd}$ Drug Group" probability (60%) to determine an amount representative of a distribution amount having the compliance rate and its respective drug group probability applied to it. Alternatively, if 100% of members 2 participating in the shared savings prescription plan utilize "1$^{st}$ Drug Group" 68, then the estimated distribution amount, adjusted for the compliance rate (70%), is $12,022.99.

To allow the optimal sharing mix of the savings to be realized, the method also takes into account how much of the average savings the insuring entity 10 allocates to members 2. This amount is represented by a member share rate, as shown in Table 1, which may be predetermined by insuring entity 10. After determining the compliance rate and, optionally, either "1$^{st}$ Drug Group" probability or "2$^{nd}$ Drug Group" probability, the member share rate is multiplied with the estimated distribution amount. This results in obtaining member amounts representative of the savings realized by all members 2 who utilized either "1$^{st}$ Drug Group" 68 or "2$^{nd}$ Drug Group" 70 in the shared savings prescription plan. Accordingly, an increase or decrease in the member share rate will increase or decrease, respectively, the amount of the average savings that is passed on to members 2.

For example, suppose member share rate is 45%, as shown in Table 1. The member amount is determined by multiplying the distribution amount having the compliance rate and the drug group probability applied to it, e.g., $4,809.20, realized by members 2 who utilized "1$^{st}$ Drug Group" 68, by member share rate, i.e., 45%. Thus, member amount is $2,164.14, which, divided by the number of individual members 2 utilizing the "1$^{st}$ Drug Group" 68, yields the average savings per member 2. For example, if there are 100 members 2 in the shared prescription savings plan utilizing "1$^{st}$ Drug Group" 68, the average member amount is $21.64, i.e., $2,164.14÷100. Similarly, the average savings per member 2 can also be determined for those members 2 utilizing "2$^{nd}$ Drug Group" 70. Thus, the average member amount provides entity 10 and/or members 2 with an objective and comparative view of the cost savings when utilizing one drug group over another drug group. Other information may be derived from member amounts, including, but not limited to, estimated costs and savings per prescription for all members, individual members, and for the plan. Those of ordinary skill in the art would understand the necessary calculations required to obtain the aforementioned data. Additionally, an average per prescription incentive in terms of annual savings realized for both an individual member and/or for the plan per member may be computed. For example, the annual cost savings realized for all members in the plan is summed with total annual member paid amount 62, the sum of which is divided by the annual number of prescriptions prescribed in the plan. This results in the average per prescription incentive per member, which may be used to induce members to utilize a drug plan other than that embodied in summary data 42.

As previously mentioned, insuring entity 10 contracts with plan facilitator 12 and negotiates a commission to be paid to plan facilitator 12. In the desirable embodiment, the commission is based on predetermined criteria including, but not limited to, a per prescription basis or a per member per year or month basis. The commission rate of plan facilitator 12 is multiplied to the distribution amount having the compliance rate and the drug group probability applied to obtain a plan facilitator amount. The plan facilitator amount represents plan facilitator's 12 commission for facilitating the shared savings prescription plan. For example, suppose plan facilitator's 12 commission rate is 15%, as shown in Table 1. The distribution amount having the compliance rate and the drug group probability applied when "1$^{st}$ Drug Group" 68 is utilized, is $4,809.20. Thus, 15% of this distribution amount is $721.38, which is the plan facilitator amount realized when utilizing the "1$^{st}$ Drug Group" 68.

Cost savings amounts may also be determined for other participants of the shared savings prescription plan, including, but not limited to, physician amounts, pharmaceutical entity amounts, and benefits managing entity amounts. These cost savings amounts are determined by applying the estimated distribution amount to the respective percentages outlined in Table 1.

Finally, the optimal sharing mix of the savings may be determined by modifying compliance rate, member share rate, drug group probabilities, and/or any other variable data. Utilizing different data yields different member amounts. Thus, the change in member amounts also results in changes to related items, such as estimated costs and savings per prescription for all members, individual members, and for the plan. Additionally, introducing or adjusting member co-payments may additionally affect the overall costs and savings to the members and to the plan. Accordingly, modifications may result in new sharing mixes, including data sets containing new empirical data. As previously mentioned in connection with FIG. 3, empirical data may then be utilized to empirically determine the shape and location of inverse Laffer Curve 20. By analyzing the empirical data in the context of inverse Laffer Curve 20, the optimal sharing mix in a shared prescription plan may be determined. For example, as the member share rate, represented by member curve 14, is incrementally increased, the group prescription cost, represented by Laffer Curve 20, will decrease. At the point where the group prescription cost begins to increase, the optimal member share rate is determined. Desirably, the actual savings amount distributed to a particular member is pro rata proportional to the amount that member saved in relation to the original prescription they were prescribed, subject to the plan facilitator amount determined by the commission rate.

Desirably, the present invention is embodied in computer readable program code which executes on a processor of one or more stand-alone or networked computers. Each computer includes a processor, computer storage, an input/output system, a media drive, such as a disk drive, CD-ROM drive, etc., and a computer-usable storage medium capable of storing the computer software that embodies the present invention. Under the control of the computer readable program code, the processor is capable of configuring and operating the computer system in a manner to implement the present invention. Computer systems of the type described above are well known in the art and are not described herein for the purpose of simplicity.

In operation, the computer readable program code causes the processor to execute the method described above, so as for any of the empirical data to be organized and displayed in an easily understandable format, i.e., such as in a spreadsheet layout. It is to be understood that the format and the empirical data therein may either be locally or remotely accessed. Preferably, the format is conducive to real-time and interactive updates so that insuring entity 10 is able to modify any of the variable data and immediately view the changed empirical data. More specifically, any assumptions and estimates made as to the variable data allows projections of potential savings for members 2 and the plan, and, therefore, insuring entity 10 to be quickly illustrated. It is to be understood that different display formats would target various audiences. Thus, for example, the data presented to insuring entity 10, would not be the same as the data presented to members 2, as the members would only be interested in the general range of shared savings that they would enjoy. Furthermore, it is to be understood that the variable data may also be the drug data included in summary data 42 and drug groups 68 and 70. Such drug data may be dynamically updated by pharmaceutical benefits managing entity 8 so that insuring entity 10 will have the most current pricing schedules for each of the offered prescriptions when insuring entity 10 determines the optimal sharing mix.

The invention has been described with reference to the desirable embodiments. Obvious modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A computer-implemented method for determining an optimal sharing mix in a shared savings prescription plan, comprising:
    (a) storing in a computer storage of a computer a first drug group and a second drug group, wherein the drugs of the first drug group and the drugs of the second drug group are at least one of the following: formulary, chemical, physical, or therapeutic equivalents of each other, and the first and second drug groups each include one or more prescriptions;
    (b) a processor of the computer determining a total estimated cost to an insuring entity for the first drug group and a total estimated cost to the insuring entity for the second drug group;
    (c) the processor of the computer determining a first estimated savings rate associated with utilizing the second drug group versus the first drug group;
    (d) the processor of the computer determining a first estimated distribution amount as a function of the first estimated savings rate and the total estimated cost to the insuring entity for the first drug group;
    (e) the processor of the computer allocating the first estimated distribution amount to at least one of the following: the insuring entity, at least one member entity insured by the insuring entity, a plan facilitating entity, and a physician entity based upon one or more predetermined percentages; and
    (f) the processor of the computer determining an estimated physician entity amount and distributing the estimated physician entity amount to a designee of the physician entity wherein the physician entity is participating in the shared savings prescription plan, and wherein the estimated physician entity amount is determined as a function of the first estimated distribution amount and a physician entity share rate.

2. The computer-implemented method of claim 1, further comprising at least one of the following steps:
    (g) the processor of the computer determining an estimated insuring entity amount to be distributed to the insuring entity upon election by the insuring entity to participate in the shared savings prescription plan, wherein the estimated insuring entity amount is determined as a function of the first estimated distribution amount and an insuring entity share rate;
    (h) the processor of the computer determining an estimated member entity amount to be distributed to the member entity in the form of a credit, cash, or a check upon election by the member entity to participate in the shared savings prescription plan, wherein the estimated member entity amount is determined as a function of the first estimated distribution amount and a member entity share rate; and
    (i) the processor of the computer determining an estimated plan facilitating entity amount for distribution to the plan facilitating entity upon election by the plan facilitating entity to participate in the shared savings prescription plan, wherein the estimated plan facilitating entity amount is determined as a function of the first estimated distribution amount and a commission rate.

3. The computer-implemented method of claim 2, wherein at least one of the insuring entity amount, the member entity amount, the plan facilitating entity amount, and the physician entity amount is distributed to the insuring entity, the member entity, the plan facilitating entity, and the physician entity, respectively.

4. The computer-implemented method of claim 1, wherein:
    the total estimated cost to the insuring entity for the first drug group is determined by summing costs of all prescriptions prescribed in the first drug group; and
    the total estimated cost to the insuring entity for the second drug group is determined by summing estimated costs of the drugs in the second drug group.

5. The computer-implemented method of claim 4, wherein the first estimated savings rate is determined by taking a difference between the total estimated cost to the insuring entity for the second drug group and the total estimated cost to the insuring entity for the first drug group and dividing said difference by the total estimated cost to the insuring entity for the first drug group.

6. The computer-implemented method of claim 5, wherein the first estimated distribution amount is determined by multiplying the first estimated savings rate by the total estimated cost to the insuring entity for the first drug group.

7. The computer-implemented method of claim 1, wherein the first estimated distribution amount is representative of savings realized over a predetermined period of time by utilizing the second drug group versus the first drug group.

8. The computer-implemented method of claim 1, further comprising the processor of the computer facilitating a co-payment from the member entity to a pharmaceutical entity.

9. A computer-readable medium having stored thereon instructions which, when executed by a processor of a computer, causes the processor to:

identify a first drug group and a second drug group stored in a computer storage of the computer, wherein the drugs of the first drug group and the drugs of the second drug group are one of the following: formulary, chemical, physical or therapeutic equivalents of each other, and the first and second drug groups each include one or more prescriptions;

determine a total estimated cost to an insuring entity for the first drug group and a total estimated cost to the insuring entity for the second drug group;

determine a first estimated savings rate associated with utilizing the second drug group versus the first drug group;

determine a first estimated distribution amount as a function of the first estimated savings rate and the total estimated cost to the insuring entity for the first drug group; and allocate the first estimated distribution amount to a designee of a physician entity and at least one of the following: the insuring entity, at least one member entity insured by the insuring entity or a plan facilitating entity, based upon one or more predetermined percentages.

10. The computer-readable medium of claim 9, wherein the instructions further cause the processor to:

determine an estimated insuring entity amount as a function of the first estimated distribution amount and an insuring entity share rate;

determine an estimated member entity amount as a function of the first estimated distribution amount and a member entity share rate;

determine an estimated plan facilitating entity amount as a function of the first estimated distribution amount and a commission rate; and determine an estimated physician entity amount as a function of the first estimated distribution amount and a physician entity share rate.

11. The computer-readable medium of claim 10, wherein the estimated insuring entity amount, the estimated member entity amount, and the estimated plan facilitating entity amount, and the estimated physician entity amount are distributed to the insuring entity, the at least one member entity, the plan facilitating entity, and the designee of the physician entity, respectively.

12. The computer-readable medium of claim 10, wherein the instructions further cause the processor to perform the step of displaying at least one of the estimated entity amounts.

13. A computer-implemented method for determining an optimal sharing mix in a shared savings prescription plan, comprising:

(a) storing in a computer storage of a computer a first drug group and a plurality of second drug groups, wherein the drugs of the first drug group and the drugs of each second drug group are at least one of the following: formulary, chemical, physical, or therapeutic equivalents of each other, and the first and second drug groups each include one or more prescriptions;

(b) a processor of the computer determining a total estimated cost for the first drug group and a total estimated cost for each second drug group;

(c) the processor of the computer determining for each second drug group an estimated savings rate associated with utilizing the second drug group versus the first drug group;

(d) the processor of the computer determining for each second drug group an estimated distribution amount for the second drug group as a function of the estimated savings rate for the second drug group and the total estimated cost for the first drug group;

(e) the processor of the computer allocating the estimated distribution amount for each second drug group to plural entities based upon a predetermined percentage for each entity; and (f) the processor of the computer determining for each entity an estimated entity amount to be distributed to said entity or said entity's designee upon election by said entity to participate in a shared savings prescription plan for one of the second drug groups, wherein the estimated entity amount is determined as a function of a share rate for said entity and the estimated distribution amount determined for the second drug group of the elected plan, wherein one of said entities is a physician and said physician's estimated entity amount is distributed to a designee of said physician.

14. The computer-implemented method of claim 13, further comprising:

(g) storing in the computer storage a compliance rate representative of an estimated percentage of members that comprise one of said entities that are likely to participate in the shared savings prescription plan;

(h) storing in the computer storage for each second drug group a probability representative of an estimated percentage chance that the second drug group will be chosen by said members;

(i) the processor of the computer modifying the estimated distribution amount for each second drug group as a function of the compliance rate, the probability determined for the second drug group in step (h), and the estimated distribution amount determined for the second drug group in step (d); and (j) the processor of the computer allocating each estimated distribution amount determined in step (i) to the plural entities based on the predetermined percentage for each entity, wherein the estimated entity amount in step (f) is determined as a function of either the estimated distribution amount determined in step (d) or the estimated distribution amount determined in step (i).

15. The computer-implemented method of claim 14, wherein the plural entities further include:

an insuring entity; and a plan facilitating entity.

16. The computer-implemented method of claim 14, further comprising:

(k) adjusting in the computer storage the probability for each second drug group;

(l) the processor of the computer modifying the estimated distribution amount for each second drug group as a function of the adjusted probability for the second drug group in step (k); and (m) the processor of the computer allocating each estimated distribution amount determined in step (l) to the plural entities based on the predetermined percentage for each entity, wherein the estimated entity amount in step (f) is determined as a function of either the estimated distribution amount determined in step (d), the estimated distribution amount determined in step (i), or the estimated distribution amount determined in step (l).

17. The computer-implemented method of claim 1, wherein the first drug group is comprised of plural prescription drugs that were acquired over a predetermined time interval.

18. The computer-implemented method of claim 13, wherein one of said entities includes at least one member and said member's estimated entity amount is distributed to said member in the form of a credit, cash, or a check.

19. The computer-implemented method of claim 13, further comprising:

incrementally adjusting a share rate of one of said plural entities until a total estimated cost to another of said plural entities is minimized, wherein said adjusting results in modification of the estimated entity amount to be distributed to each of said plural entities; and distributing to at least one of said plural entities, said entity's modified estimated entity amount.

20. The computer-implemented method of claim 13, further including the processor of the computer modifying the estimated distribution amount for each second drug group by a compliance rate and a probability, wherein the compliance rate is representative of an estimated percentage of members that comprise one of said entities that are likely to participate in the shared savings prescription plan, and the probability is representative of an estimated percentage chance that the second drug group will be chosen by said members, and wherein the estimated physician entity amount to be distributed in step (f) is determined as a function of either the modified estimated distribution amount or the estimated distribution amount determined in step (d).

21. The computer-implemented method of claim 20, further comprising the processor of the computer incrementally adjusting a savings share rate for said members until a weighted average estimated distribution amount for all of the second drug groups is maximized.

\* \* \* \* \*

UNITED STATES PATENT AND TRADEMARK OFFICE
CERTIFICATE OF CORRECTION

| | | |
|---|---|---|
| PATENT NO. | : 7,640,177 B2 | Page 1 of 1 |
| APPLICATION NO. | : 10/609995 | |
| DATED | : December 29, 2009 | |
| INVENTOR(S) | : Donald R. Fralic | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1947 days.

Signed and Sealed this

Ninth Day of November, 2010

David J. Kappos
*Director of the United States Patent and Trademark Office*